US008372452B2

(12) United States Patent (10) Patent No.: US 8,372,452 B2
Chauhan et al. (45) Date of Patent: Feb. 12, 2013

(54) ORAL HERBAL COMPOSITION FOR THE TREATMENT OF ORAL CANDIDIASIS

(75) Inventors: Vijay Singh Chauhan, Mumbai (IN); Kavita Sujeet Salkar, Mumbai (IN)

(73) Assignee: Piramal Life Sciences Limited, Mumbai (IN)

( * ) Notice: Subject to any disclaimer, the term of this patent is extended or adjusted under 35 U.S.C. 154(b) by 0 days.

(21) Appl. No.: 13/001,268

(22) PCT Filed: Jun. 25, 2009

(86) PCT No.: PCT/IB2009/052741
§ 371 (c)(1),
(2), (4) Date: Dec. 23, 2010

(87) PCT Pub. No.: WO2009/156962
PCT Pub. Date: Dec. 30, 2009

(65) Prior Publication Data
US 2011/0111067 A1 May 12, 2011

(30) Foreign Application Priority Data
Jun. 26, 2008 (IN) .......................... 1340/MUM/2008

(51) Int. Cl.
*A61K 36/67* (2006.01)
*A61K 36/00* (2006.01)
(52) U.S. Cl. .......................... 424/734; 424/725; 424/777
(58) Field of Classification Search .................. None
See application file for complete search history.

(56) References Cited

U.S. PATENT DOCUMENTS

| 4,624,849 | A  | * | 11/1986 | Toogood ........................ 514/358 |
| 7,482,031 | B2 | * | 1/2009 | Pushpangadan et al. ..... 424/734 |
| 2004/0126441 | A1 |  | 7/2004 | Pushpangadan et al. |
| 2006/0257507 | A1 | * | 11/2006 | Doshi et al. .................. 424/734 |
| 2011/0135760 | A1 | * | 6/2011 | Kreuter et al. ................ 424/734 |

FOREIGN PATENT DOCUMENTS

| JP | 56-083416 A | 7/1981 |
| JP | 2001-278800 A | 10/2001 |
| JP | 2003-089652 A | 3/2003 |
| WO | 2004/058283 A1 | 7/2004 |
| WO | WO 2004/058283 A1 * | 7/2004 |

OTHER PUBLICATIONS

Thefreedictionary.com. Retrieved from the internet. <http://www.thefreedictionary.com/lozenge>. Retrieved on Dec. 13, 2011. 2 Pages.*
Weiss. Spice Crops. CABI, Jul. 1, 2002. p. 182.*
Guenther. Properties and Uses of Ol Cubeb. The American Perfumer and Essential Oil Review. 1942. 44 (No. 7). Pages 43, 45, and 47.*
Jain et al. Antibacterial Evaluation of Some Indigenous Volatile Oils. Planta Medica. vol. 26. 1974.*
Silva, M. L. A. et al. "Evaluation of Piper cubeba Extract, (−)-Cubebin and its Semi-synthetic Derivatives against Oral Pathogens," Phytotherapy Research, Published online Jan. 18, 2007, vol. 21, pp. 420-422.
Chatterjee, A. et al. "Spectral Properties of Cubebin," Journal Indian Chem. Soc., Received Oct. 23, 1967, vol. 45, No. 8, pp. 723-725.
Morace, G. et al. "Epidemiological and Clinical Aspects of Mycoses in Patients with AIDS-Related Pathologies," European Journal of Epidemiology, Dec. 1990, vol. 6, No. 4, pp. 398-403.
Gravina, Haylen Gonzalez et al. "Oral Candidiasis in children and adolescents with cancer. Identification of *Candida* spp," Med Oral Patrol Oral Cir Bucal, Oct. 1, 2007, vol. 12, No. 6, pp. E419-E423.
Law, D. et al. "High prevalence of antifungal resistance in *Candida* spp. from patients with AIDS," Journal of Antimicrobial Chemotherapy, revised version accepted Aug. 2, 1994, vol. 34, pp. 659-668.
Cowen, Leah E. et al. "Evolution of Drug Resistance in Experimental Populations of *Candida albicans*," Journal of Bateriology, Mar. 2000, vol. 182, No. 6, pp. 1515-1522.
Canuto Masia et al. "Epidemiology of yeast colonization and oropharyngeal infection other than *Candida albicans* in patients with HIV infection," Med Clin (Barcelona), Feb. 20, 1999, vol. 112, No. 6, pp. 211-214.
Lieberman, A. A. Pharmaceutical Dosage Forms: Tablets, 1980, vol. 1, p. 339, p. 469.
Marr, Kieren A. et al. "Rapid, Transient Fluconazole Resistance in *Candida albicans* Is Associated with Increased mRNA Levels of CDR," Antimicrobial Agents and Chemotherapy, Oct. 1998, vol. 42, No. 10, pp. 2584-2589.
International Search Report of PCT/IB2009/052741, mailing date Sep. 29, 2009.
Written Opinion of PCT/IB2009/052741, mailing date Sep. 29, 2009.

* cited by examiner

*Primary Examiner* — Christopher R. Tate
(74) *Attorney, Agent, or Firm* — Westerman, Hattori, Daniels & Adrian, LLP

(57) ABSTRACT

An oral herbal composition comprising a therapeutically effective amount of an extract derived from the berries of a plant, *Piper cubeba*, wherein the composition is provided for use in the treatment of oral candidiasis (oral thrush). The oral herbal composition can be formulated in the form of a candy, a chewable tablet and an oral gel. The herbal composition exhibits antifungal activity against azole resistant strains of *Candida albicans*. The herbal composition is safe to administer and has improved patient compliance.

17 Claims, No Drawings

ORAL HERBAL COMPOSITION FOR THE TREATMENT OF ORAL CANDIDIASIS

FIELD OF INVENTION

The present invention relates to an oral herbal composition for use in the treatment of diseases of oral cavity, which composition comprising a therapeutically effective amount of an extract of a plant, Piper cubeba (P. cubeba). More specifically the invention relates to an oral herbal composition for use in the treatment of oral candidiasis or oral thrush, which composition comprising a therapeutically effective amount of an extract of a plant, Piper cubeba (P. cubeba). The present invention also provides a process for manufacture of the oral herbal composition.

BACKGROUND OF THE INVENTION

Candidiasis (yeast infection or thrush) is a fungal infection (mycosis) caused by a member of the Candida species. Candida yeasts are usually present in most people, but their uncontrolled multiplication can result in infection of the mouth, skin or vagina. The overgrowth of Candida yeasts is kept in check by other naturally occurring microorganisms, e.g. bacteria co-existing with the yeasts in the same locations, and by the human immune system. One of the common causes of candidiasis may be the frequent use of antibiotics that are clinically expected to destroy harmful and disease causing microorganisms in the body, but they may also destroy the beneficial microorganisms which are responsible for keeping the growth of yeasts (fungi) in check. The destruction of beneficial microorganisms may cause the yeasts (fungi) to grow out of control resulting in condition known as candidiasis moniliasis, or a "yeast" infection. A weakened or undeveloped immune system or metabolic disorders, such as diabetes may also predispose individuals to Candidiasis.

Oral candidiasis (oral thrush) is the most common fungal infection in the mucous membranes of the mouth. Although oral thrush can affect anyone but it is more prevalent in babies and toddlers, people who wear dentures, and in people with compromised immune systems, especially those suffering from acquired immune deficiency syndrome (AIDS), cancer patients undergoing chemotherapy and those who have undergone bone marrow transplantation or solid organ transplantation or other immunocompromised patients. As indicated herein above, the disease causing pathogen is usually Candida species (fungi). Most commonly, oral candidiasis is caused by Candida albicans (C. albicans), however, the emergence of other species of Candida causing oral candidiasis have been reported. In a relatively recent report of 153 HIV-positive patients, it was described that 21% of the patients had oral candidiasis caused due to non-Candida albicans species, the most common of which was Candida glabrata (Masia Canuto et al.; Med. Clin. 112:211-214, (1999)). Similarly, it was also found that 25% of the yeast species isolated from persons with AIDS were non-Candida albicans species (Morace G. et al; Eur. J. Epidemiol. 6:398-403 (1990)). In a most recent study involving detection and identification of Candida species responsible for causing oral candidiasis in children and adolescents having cancer, it was found that although C. albicans was the most common species, other species namely Candida parapsilosis (C. parapsilosis), Candida tropicalis (C. tropicalis), Candida krusei (C. krusei), Candida glabrata (C. glabrata) and Candida lusitaniae (C. lusitaniae) were also responsible for causing oral candidiasis (Med. Oral. Patol. Oral. Cir. Bucal; 2007 Oct. 1; 12(6); E419-23 (2007). The most common symptoms of oral candidiasis are discomfort and burning of the mouth and throat and an altered sense of taste. Oral candidiasis is characterised by the appearance of whitish velvety plaques on the mucous membrane of the mouth and tongue, and scraping of this whitish material reveals a red (erythematous) rash underneath with pinpoint bleeding. In immunocompromised people, the infection may be massive and in addition it may spread to the esophagus producing candidal esophagitis causing pain in the mouth and eventually resulting in painful difficult swallowing.

The standard therapy for the treatment of oral candidiasis involves use of antifungal agents selected from polyene derivatives such as amphotericin B and the structurally related compound, nystatin (mycostatin); and the azole antifungal agents such as miconazole, ketaconazole, fluconazole, itraconazole or clotriamazole. However, there are limitations to the use of these synthetic antifungal agents in terms of their poor safety profile, multiple drug-drug interactions, excessive cost and lack of efficacy due to the growing resistance of Candida species to the conventional antifungal agents.

The prevalence of resistance of the Candida species, especially C. albicans isolated from patients with AIDS, to antifungal agents namely amphotericin B and fluconazole have been reported (Law D. et al., J. Antimicro. Chemo (1994) 34, 659-668). The evolution of resistance of candida species particularly the experimental population of C. albicans to azole antifungal agents, especially fluconazole, ketoconazole and itraconazole (Leah E. Cowen et al., J. Bacteriology, March 2000, 182 (6), p. 1515-1522) further renders the treatment less effective. Also, evidences indicate that fluconazole resistant C. albicans, can be a cause of recurrent oral candidiasis in patients with HIV infection, patients receiving cancer chemotherapy and patients who have undergone bone marrow transplantation or solid organ transplantation (Kieren A. Marr et al., Antimicrobial Agents and Chemotherapy, Oct. 1998; 42(10): 2584-2589).

Use of alternative therapies, particularly herbal-based therapies, is gaining momentum throughout the world. Several plants, plant extracts or substances derived from plants have been used for years to treat a wide range of diseases. The use of herbal compositions for the treatment of diseases of the oral cavity is known in the art and is gaining increased importance. Essential oils extracted from herbs have been provided for use in complementary medicine for bacterial and fungal infections. Japanese Patent Application no. 2003089652A relates to an herbal composition for preventing the onset of and for the treatment of oral candidiasis (oral thrush). The composition comprises of blends of various essential oils as active ingredients, which are selected from tea tree oil, Shinsei lavender oil, French lavender oil, spike lavender oil, the attar of rose, geranium oil, patchouli oil, lemon GURASU oil and palmarosa oil. The essential oil components are terpinene-4-ol, linalool, citranellol, geraniol, citral, citronellal and hinokitiol.

The plant, Piper cubeba L. (P. cubeba), commonly known as Kababchini (in India) belongs to Piperaceae family. The P. cubeba plant has been widely used in Asia as a condiment, food additive and a soothing agent for burning throat and for treating coughs. Use of the P. cubeba extract in combination with other plant extracts in the treatment of certain medical ailments is reported in the art. For instance, U.S. Published Patent Appln. No. 20040126441 A1 teaches a synergistic herbal composition comprising extracts of P. cubeba, Glycyrrhiza glabra, Acorus calamus Alpinia galanga, Zingiber officinale along with pharmaceutically acceptable additives for use as an anti-cough, anti-tussive, and throat soothing formulation. JP Published Patent Appln. No. 56083416A relates to a composition for oral cavity for preventing dental caries and pyorrhea alveolaris, wherein the composition comprises one or more materials extracted with organic solvents from plants selected from the group consisting of *Ginkyo biloba* L., *Anethum graveolens* L., *Piper Cubeba* L., *Nardostachys jatamansi* DC, *Zingiber officinale* Roscoe, *Asiasarum Sieboldi* F. Maekawa, *Bupleurum Falcatum* L., *Malva silvestris* L., *Caesalpinia sappan* L., *Terminalia charbrila* Rety, etc. Japanese Published Patent Appln No. 2001278800A relates to a cariostatic agent (anti-caries agent) containing at least one extract of a plant selected from Sariawan (*Olygala glomerata* Lour) or Kemukus (*P. cubeba* L) wherein the cariostatic agent is formulated as a composition for use as a mouthwash and also as an additive in food or a drink to prevent diseases of oral cavity, especially dental plaque. A study report (Silva M L et al., Phytotherapy Research, 2007, 21(5): 420-2) discloses activity of an ethanolic extract of *P. cubeba* against oral pathogens (microorganisms). The microorganisms used in the study included *Enterococcus faecalis, Streptococcus salivarius, Streptococcus mitis, Streptococcus mutans, Streptococcus sobrinus, Streptococcus sanguinis* and *C. albicans*. According to the report, the crude ethanolic extract from *P. cubeba* seeds, (-)-cubebin and its semi-synthetic derivatives exhibited activity against said microorganisms. The crude extract was found to be most active against *Streptococcus salivarius*.

It is evident from the current art that there still exists a long felt need and a strong demand for an oral composition for the treatment of oral candidiasis, which can combat the adverse side effects associated with synthetic drugs, overcome the problem of resistance to conventional antifungal agents and also provide additional benefits. The present invention provides a solution to this problem in the form of an oral herbal composition which can fulfill the widely recognized need by providing an effective and safe treatment for oral candidiasis. The herbal composition also delivers other additional organoleptic benefits.

OBJECTS OF THE INVENTION

Accordingly, an object of the present invention is to provide an oral herbal composition for use in the treatment of oral candidiasis (oral thrush), wherein the composition comprises a therapeutically effective amount of an extract of a plant, *P. cubeba*.

Another object of the invention is to provide an oral herbal composition for use in the treatment of oral candidiasis (oral thrush), wherein the composition comprises a therapeutically effective amount of *P. cubeba* extract along with at least one pharmaceutically acceptable excipient.

Another further object of the invention is to provide an oral herbal composition for use in the treatment of azole resistant oral candidiasis, wherein the composition comprises a therapeutically effective amount of *P. cubeba* extract along with at least one pharmaceutically acceptable excipient.

Another object of the invention is to provide an oral herbal composition for use in the treatment of oral candidiasis, wherein the composition comprises a therapeutically effective amount of *P. cubeba* extract, exhibiting improved patient compliance.

Yet another object of the invention is to provide a process for manufacture of an oral herbal composition comprising the steps of obtaining the plant extract of *P. cubeba* and formulating said extract with one or more pharmaceutically acceptable excipients.

Yet another object of the invention is to provide a method for the treatment of oral candidiasis in a subject, wherein the method comprises administering to the subject in need thereof a therapeutically effective amount of an oral herbal composition comprising a therapeutically effective amount of *P. cubeba* extract and at least one pharmaceutically acceptable excipient.

Various objects and advantages of the present invention will become apparent from the detailed description of the invention.

SUMMARY OF THE INVENTION

The present invention provides an oral herbal composition for use in the treatment of oral candidiasis (oral thrush), wherein said composition comprises a therapeutically effective amount of an extract of a plant, *P. cubeba* and at least one pharmaceutically acceptable excipient.

The oral herbal composition of the present invention may be formulated in the form of a candy, a chewable tablet and an oral gel. The oral herbal composition is provided for use in the treatment of azole resistant oral candidiasis.

In one aspect, the present invention provides a process for manufacture of an oral herbal composition, wherein said method comprises the steps of:
    a) obtaining the berries of *P. cubeba*;
    b) drying the *P. cubeba* berries in shade;
    c) pulverising the dried *P. cubeba* berries to obtain a fine powder;
    d) extracting repeatedly the fine powder obtained in step (c) with a non-polar solvent;
    e) concentrating the extract under vacuum to obtain a concentrated liquid extract in viscous oil form; and
    f) formulating the extract which is in viscous oil form with one or more pharmaceutically acceptable excipients to obtain the herbal composition.

In another aspect, the present invention provides a method for the treatment of oral candidiasis in a subject wherein the method comprises administering to the subject in need thereof a therapeutically effective amount of oral herbal composition comprising a therapeutically effective amount of *P. cubeba* extract and at least one pharmaceutically acceptable excipient.

DETAILED DESCRIPTION OF THE INVENTION

The present invention provides an oral herbal composition which comprises a therapeutically effective amount of an extract derived from the plant, *P. cubeba*, particularly from the berries of the plant, wherein said composition is provided for use in the treatment of oral candidiasis. The herbal composition may be formulated in the form of a candy, a chewable tablet and an oral gel. The herbal composition of the present invention comprises the *P. cubeba* extract as the active ingredient and suitable pharmaceutically acceptable excipients to be formulated in a desired form.

Accordingly, the oral herbal composition of the present invention comprises a therapeutically effective amount of an extract derived from the berries of the plant, *P. cubeba*, wherein said composition is provided for use in the safe and effective treatment of oral candidiasis.

It has been indicated herein above, that *C. albicans* is the most common *candida* species that is the causative pathogen for oral candidiasis. However, other *candida* species, especially *C. glabrata* and *C. krusei* have also been reported to cause oral candidiasis. Accordingly, the herbal composition of the present invention is provided for use in the treatment of oral candidiasis caused by *candida* species selected from the group consisting of *C. albicans*, *C. krusei* and *C. glabrata*.

The extract derived from the berries of the plant, *P. cubeba* contained in the herbal composition of the present invention also exhibits antifungal activity against azole resistant strains of *candida* species including *C. albicans*. Accordingly, the herbal composition of the present invention is provided for use in the treatment of azole resistant oral candidiasis.

The following is a list of definitions for terms used herein. These definitions apply to the terms as they are used throughout the specification unless otherwise limited in specific instances.

The term "therapeutically effective amount" as used herein means an amount of an active ingredient i.e., *P. cubeba* extract to be incorporated in the herbal composition which is sufficient enough to exhibit antifungal activity and significantly improves the condition to be treated, i.e., oral candidiasis (oral thrush) but low enough to avoid side effects, if any (at a reasonable benefit/risk ratio), within the scope of a sound medical judgment.

The term "extract" as used herein is intended to mean a concentrate of the extract components derived from the berries of the *P. cubeba* plant. Also, the terms "extract of the plant, *P. cubeba*", "*P. cubeba* extract" and "the extract" are used interchangeably.

The term "chewable" as used herein refers to the herbal composition in a form which may be chewed in the mouth to obtain the desired pharmacological result without the need to swallow the entire tablet.

The term "Minimum inhibitory concentration (MIC)" is defined as the lowest concentration of the *P. cubeba* extract exhibiting no visible growth or causing almost complete inhibition of growth of the *Candida* species.

As used in the specification, percentage values (%) represent the weight percentage based on the total weight of the composition.

As used in the specification, the term "about" means approximately and in the context of numerical values the term "about" may be construed to estimate a value that is ±10% of the value or range recited.

As used in the specification, the singular forms "a," "an," and "the" include plural referents unless the content clearly dictates otherwise.

The plant extract incorporated in the herbal composition of the present invention is an extract derived from the berries of the plant, *P. cubeba*. The extract from the berries of the plant, *P. cubeba* is obtained using a non-polar solvent. The *P. cubeba* extract is obtained in a viscous oil form and has a characteristic odour. The extract exhibits antifungal activity against *Candida albicans*. Other *candida* species against which the extract is found to exhibit antifungal activity are *C. krusei* and *C. glabrata*. Accordingly, the herbal composition of the present invention can be used for the treatment of oral candidiasis which is caused by candida species selected from the group consisting of *C. albicans*, *C. krusei* and *C. glabrata*.

The *P. cubeba* extract is also effective against azole resistant strains of *candida* species including *C. albicans*, *C. krusei* and *C. glabrata*. Accordingly, the herbal composition of the present invention can be used for the treatment of oral candidiasis, which is an azole resistant oral candidiasis.

In an embodiment of the present invention, the oral herbal composition provided for use in the treatment of oral candidiasis, comprises 0.05 to 20% of the *P. cubeba* extract based on the total weight of the composition.

Another embodiment of the present invention provides a process for manufacture of an oral herbal composition wherein said process comprises the steps of:

a) obtaining the berries of *P. cubeba*;
b) drying the *P. cubeba* berries in shade;
c) pulverising the dried berries of *P. cubeba* to obtain a fine powder;
d) extracting repeatedly the fine powder obtained in step (c) with a non-polar solvent;
e) concentrating the extract under vacuum to obtain a concentrated liquid extract in viscous oil form; and
f) formulating the extract which is in viscous oil form with pharmaceutically acceptable excipients to obtain the herbal composition.

The non-polar solvent used in the extraction process of the present invention is selected from a group consisting of petroleum ether, n-hexane, toluene, n-heptane, chloroform. As a representative example of the non-polar solvents, petroleum ether is used for the extraction of the fine powder of *P. cubeba* berries.

The extraction of the fine powder of dried berries of *P. cubeba* is carried out using the non-polar solvent in an amount sufficient to obtain the extract in viscous oil form.

The extraction is carried out at a temperature of about 35° C. to 40° C. and a pressure of about 1 atmosphere.

In an embodiment of the present invention, the oral herbal composition for use in the treatment of oral candidiasis, comprises a therapeutically effective amount of *P. cubeba* extract in viscous oil form and at least one pharmaceutically acceptable excipient.

In another embodiment of the present invention, the extract which is in viscous oil form, is formulated with one or more pharmaceutically acceptable excipients to obtain the herbal composition in the form of a chewable tablet, an oral gel and a candy.

According to a particular embodiment of the invention, the oral herbal composition is prepared as a candy that comprises 0.05 to 5% of the *P. cubeba* extract in viscous oil form. The herbal composition of the present invention in the form of a candy is preferable as the candy is retained in the oral cavity for substantial period of time during consumption and therefore, it would actually make the candy containing the *P. cubeba* extract an effective remedy for the treatment of oral candidiasis.

In the process of the manufacture of the herbal composition in the form of a candy, the present inventors have observed that the physicochemical characteristics particularly the viscosity and thickness of the *P. cubeba* extract contained in the herbal composition as an active ingredient influences the effectiveness of the composition. Use of the extract in viscous oil form minimizes the chances of degradation of the active ingredient (the extract) at high temperatures since it is a known fact that preparation of a hard candy formulation involves employing very high temperatures of at least 120° C.-130° C. Thus, the non-polar solvent used for extracting berries of the *P. cubeba* plant is responsible for producing the extract in viscous oil form which in turn influences the effectiveness of the composition. The *P. cubeba* extract in viscous oil form facilitates slow release of the active ingredient in the mouth thereby ensuring that the active ingredient stays in the oral cavity for a longer period of time. The herbal composition of the present invention therefore provides a prolonged and sustained antifungal activity in the oral cavity that makes the composition much more effective for the treatment of oral candidiasis.

Candy is a confectionary product. A hard-boiled confectionary has a hard texture, glassy appearance and a solids content of 97-98%. The hard-boiled candy generally comprises a confectionary base composed of a mixture of up to about 70% sugar (sucrose) and other carbohydrate bulking agents and usually up to about 92% corn syrup. Non-fermentable sugars such as sorbitol, mannitol, xylitol, maltitol, isomalt, erythritol, etc., may also be employed. Additionally ingredients such as flavouring agents, acidulants, gelling agents, diluents, colourants, binders, humectants and preservatives may also be included. The hard confectionary may be prepared in various shapes and forms, such as flat, circular, octagonal and biconvex forms. A general discussion of the composition of hard confectionary products may be found in E. B. Jackson, Ed. "Sugar Confectionery Manufacture", second edition, Blackie Academic and Professional Press, Glasgow UK, (1990) (pages 129-169).

The preparation of confectionary products or formulations is historically well known and has changed little over the years. Such confectionary may be routinely prepared by conventional methods such as those involving use of fire cookers, vacuum cookers, and scraped-surface cookers.

If a vacuum cooker is used for the preparation of candy, the carbohydrate bulking agent is boiled to 125-132° C. in the cooker and vacuum is applied. Additional water from the cooker is boiled off without extra heating. When the cooking is complete, the mass is a semi-solid and has a plastic-like consistency. At this point, the *P. cubeba* extract, flavours, colourants, and other additives are admixed in the mass by routine mechanical mixing operations.

The optimum mixing required to uniformly mix the flavours, colourants and other additives during conventional manufacturing of hard confectionary product is determined by the time needed to obtain a uniform distribution of the materials. Once the candy mass has been properly prepared, it may be cut into workable portions or formed into desired shapes. A variety of forming techniques may be utilized depending upon the shape and size of the final product desired. A general discussion on the composition and preparation of hard confectionery products may be found in A. A. Lieberman, Pharmaceutical Dosage Forms: Tablets, Volume 1 (1980), Marcel Dekker, Inc, New York, N.Y. at pages 339, 469, the disclosure of which is incorporated herein as a reference.

Although it is preferred to have the herbal composition of the present invention in the form of a candy, the composition may also be provided in the form of a chewable tablet and an oral gel.

Formulations for chewable tablets are well known and typically contain a base of sugar, starch, or lipid and a flavoring agent. The chewable tablet of the present invention is made by any suitable process known in the art. An exemplary formulation for a chewable tablet is provided herein. The pharmaceutically acceptable additives used for the preparation of chewable tablets may be selected from among others, preservatives, binders, lubricants, sweetening agents, suitable colouring agents, flavouring agents etc. The chewable tablet comprising the *P. cubeba* extract in viscous oil form can be of any desired colour, shape and form.

The composition in the form of an oral gel may be prepared by incorporating the *P. cubeba* extract in viscous oil form with other pharmaceutically acceptable additives, wherein the composition is formulated as an oral gel using any conventional means or method. The pharmaceutically acceptable additives may be selected from preservatives, sweetening agents, flavouring agents, thickeners, humectants, solubilising agents etc. An exemplary formulation for oral gel is provided herein.

The flavoring agents that are suitable for use in this invention may be selected from among the group consisting of peppermint oil, menthol, lemon oil, orange oil, cinnamon oil etc. The sweetening agents that are suitable for use in this invention may be selected from the group consisting of sucrose, liquid glucose, sucralose, mannitol, aspartame, saccharin sodium etc.

The binders that are suitable for use in this invention may be selected from the group consisting of starch paste, sorbitol, guar gum, polyvinyl pyrrolidone, cellulose derivatives such as hydroxy propylmethyl cellulose, sodium carboxymethyl cellulose, carbomer (commercially available as carbopols) etc. The preservatives suitable for use in this invention may be selected from among the group consisting of sodium benzoate, methyl paraben, propyl paraben, cresols, etc.

The lubricants that are suitable for use in this invention may be selected from metallic stearates such as magnesium, calcium and sodium stearates, stearic acid, talc, polyethylene glycols, soluble salts such as sodium chloride, sodium benzoate etc. The humectants that are suitable for use in this invention may be selected from glycerol, sorbitol, polypropylene glycol etc. The colouring agents that are suitable for use in this invention are conventional colouring agents that have been approved for regulatory use.

In an embodiment, the present invention also relates to the use of an oral herbal composition comprising a therapeutically effective amount of the *P. cubeba* extract in viscous oil form and at least one pharmaceutically acceptable excipient, for the treatment of oral candidiasis.

In another embodiment, the present invention also relates to the use of an oral herbal composition comprising 0.05 to 20% of the *P. cubeba* extract in viscous oil form and at least one pharmaceutically acceptable excipient, for the treatment of oral candidiasis.

In yet another embodiment, the present invention relates to the use of an oral composition comprising 0.05 to 5% of the *P. cubeba* extract in viscous oil form and at least one pharmaceutically acceptable excipient, for the treatment of oral candidiasis, wherein the oral composition is formulated in the form of a candy.

In yet another further embodiment, the present invention relates to the use of an oral herbal composition comprising a therapeutically effective amount of the *P. cubeba* extract and at least one pharmaceutically acceptable excipient, for the manufacture of a medicament for the treatment of oral candidiasis.

The present invention also encompasses within its scope a method for the treatment of oral candidiasis in a subject, wherein said method comprises administering to the subject in need thereof a therapeutically effective amount of the oral herbal composition comprising a therapeutically effective amount of the *P. cubeba* extract in viscous oil form and at least one pharmaceutically acceptable excipient.

In accordance with the present invention, the desirable dose of the composition will vary depending on a number of factors including, e.g. the physical characteristics of the individual such as the age, weight and physical health, and severity of the disease and can be readily determined by a skilled medical practitioner. However, in order to obtain desirable effects, it is generally recommended to administer the composition in the form of a candy at a dosage ranging from 1 g to 35 g per day in a single dosage form or a separate multi-dosage form.

The herbal composition in other forms such as the chewable tablet and the oral gel may be taken at suitable dosage. In order to obtain desirable effects, it is generally recommended to administer the composition in the form of a chewable tablet at a dosage ranging from 0.5 g to 24 g per day in a single dosage form or a separate multi-dosage form. It is also recommended to administer the composition in the form of an oral gel (1%) at a dosage ranging from 1 g to 20 g in a single dosage form or a separate multi-dosage form.

Duration of the treatment may vary on the basis of the severity of the oral candidiasis to be treated and may extend over a period of 1 week to 1 month or even more.

The composition of the present invention provides a better alternative to existing expensive antifungal agents. More importantly, the composition is substantially free of serious adverse reactions that are caused by the conventional antifungal agents.

The following examples further describe and demonstrate embodiments within the scope of the present invention. These examples are provided for the purposes of illustration only and may not be construed to be limiting the scope of the present invention.

EXAMPLES

Example 1

Preparation of *P. cubeba* Extract

The berries of the plant, *P. cubeba* procured commercially were shade dried and coarse pulverised (6-8 mesh size) to obtain the dried berries in powdered form. The powder was refluxed with petroleum ether (60:80) at a temperature of 40±5° C. and atmospheric pressure with constant stirring and extracted repeatedly (three times) for a period of 3 hours. The extraction was carried out using the solvent in an amount two fold (weight/volume) the amount of powdered *P. cubeba* berries. The extract was filtered, concentrated under vacuum using a rotary evaporator to obtain a concentrated viscous oil form of *P. cubeba* extract. The yield of the extract varied from 10 to 18%.

Example 2

Preparation of the Herbal Composition Containing the *P. cubeba* Extract

Candy Formulation (20 Kg)

| Ingredient | Weight |
| --- | --- |
| Sugar | 13 kg |
| Liquid glucose | 7 kg |
| Citric acid | 40 g |
| *P. cubeba* extract (in viscous oil form) | 100 g |
| Flavour | 50 ml |

1. Sugar was dissolved in water, and then liquid glucose and citric acid were added to it.
2. The resulting mixture was cooked in a vacuum cooker at 120° C.
3. The boiled mixture was then taken out on a cooling sheet and *P. Cubeba* oil (100 g) and flavour (50 ml) were added to it and beaten for proper mixing to obtain a syrup.
4. The syrup was then transferred to a candy cutting machine to produce candies of desired shape. The final candy product had a glass-like translucent appearance.

Example 3a

Preparation of the Herbal Composition Containing the *P. cubeba* Extract

Oral Gel (100 g)

| Ingredient | Weight |
| --- | --- |
| Carbomer C | 1 g |
| Tween 80 | 1 g |
| Polyethylene glycol-400 (PEG-400) | 20 g |
| Propylene glycol | 2 g |
| Methyl paraben | 0.1 g |
| Phenoxy ethanol | 0.25 g |
| EDTA | 0.1 g |
| Sodium hydroxide | 0.1 g |
| Aspartame | 0.2 g |
| Water | 78 g |
| *P. cubeba* extract (in viscous oil form) | 1 g |

1. Carbomer was dispersed in water and stirred for 30 minutes to obtain a uniformly thick dispersion.
2. Sodium hydroxide (0.1 g) was dissolved in purified water (10 g) to form a solution.
3. The solution obtained in step 2 was added to the dispersion of step 1 and mixed thoroughly.
4. A solution prepared by mixing water, EDTA and aspartame was added to contents of step 3.
5. Polyethylene glycol-400 (PEG-400), propylene glycol, methyl paraben and phenoxy ethanol were added slowly to the dispersion obtained in step 4.
6. Finally *P. cubeba* extract and desired flavour was added to the dispersion obtained in step 5 and stirred to obtain a uniform gel.

Example 3b

Preparation of the Herbal Composition Containing the *P. cubeba* Extract

Chewable Tablet (1200 mg)

| Ingredient | Weight |
| --- | --- |
| Instacoat mask | 150 mg |
| Sugar | 250 mg |
| Pearlitol | 200-400 mg |
| Avicel 200ph | 78.8 mg |
| Aerosil 200 | 36 mg |
| Sucralose | 9 mg |
| Methyl paraben sodium | 2 mg |
| Propyl paraben sodium | 0.2 mg |
| Citric acid | 60 mg |
| Sodium chloride | 24 mg |
| PVP K-30 (Polyvinyl pyrrolidone) | 60 mg |
| Erythrosine colour | 2 mg |
| Isopropyl alcohol | q.s. |
| Talc | 24 mg |

-continued

| Ingredient | Weight |
|---|---|
| Peppermint | 6 mg |
| Magnesium stearate | 12 mg |
| P. cubeba extract (in viscous oil form) | 50 mg |

1. Instacoat mask was dispersed in P. cubeba extract and soaked overnight.
2. The ingredients sugar, pearlitol, avicel, aerosil, sucralose, methyl paraben sodium, propyl paraben sodium, citric acid, sodium chloride, tartaric acid, sodium citrate, polyvinyl pyrrolidone 30 and erythrosine colour were sifted through sieve mesh size 60.
3. A mass of the ingredients in step 2 was prepared using isopropyl alcohol and passed through sieve mesh size 8.
4. The mass as obtained in step 3 was then subjected to dry granulation at 50° C. to 60° C.
5. The dried granules were screened to a suitable size for compression using a sieve mesh size 30.
6. Talc, peppermint and magnesium stearate were mixed thoroughly with the granules.
7. The granulation was then compressed in to a finished tablet (1200 mg).

Example 4

In vitro Susceptibility Test (MIC) of the P. cubeba Extract by Macro Broth Dilution Method To evaluate the effectiveness of the P. cubeba extract (in viscous oil form), in vitro tests were conducted with C. albicans strains. Macro broth dilution susceptibility assay was used for determining the minimum inhibitory concentration (MIC) of the P. cubeba extract. The medium employed for the broth macro dilution method was RPMI 1640 (Sigma) with L-glutamine but without sodium bicarbonate and buffered at pH 7.0 with 3-(N-morpholino) propane sulfonic acid, monosodium salt (MOPS). The stock solution of the P. cubeba extract was prepared in 100% dimethyl sulfoxide at 100 times the final concentration, followed by further dilutions in RPMI 1640 medium to yield ten times the final strength required for the test. Aliquots (0.1 ml) of each extract were dispensed into tubes. The final concentrations of the extract varied from 0.5 to 0.01% (v/v).

A loopful of C. albicans culture from 24-hour-old slant (37° C.) was suspended in saline and vortexed for 15 seconds. The cell density of this suspension was adjusted by adding more saline and standardised to a turbidity equivalent to that of a 0.5 McFarland Standard with a spectrophotometer at 530 nm, to yield a stock inoculum suspension of $1 \times 10^6$ to $5 \times 10^6$ cells/ml. A working suspension was prepared by serial dilutions of 100 times followed by 20 times dilution of the stock solution with RPMI medium, resulting in $5 \times 10^2$ to $2.5 \times 10^2$ cells/ml. Each tube was dispensed with 0.1 ml of the P. cubeba extract (in viscous oil form) and 0.9 ml of the fungal inoculum. Growth control tubes were included and dispensed only with the diluents without the P. cubeba extract. The tubes were incubated at 37° C. for 24 hours. The positive control used was Amphotericin B. The amount of growth in the tubes containing the extract was compared visually with the amount of growth in the growth control tubes. The MIC was defined as the lowest concentration of the P. cubeba extract showing 100% inhibition of growth of the fungal C. albicans strains. The MIC of the P. cubeba extract for the C. albicans strains was found to be varying in the range of 0.12 to 0.25% (v/v).

Example 5

In Vitro Susceptibility Test (MIC) of the P. cubeba Oil Extract Against Fluconazole Resistant C. albicans Strains by Macro Broth Dilution Method The activity of the P. cubeba extract (in viscous oil form) against fluconazole resistant strains was ascertained by the macro broth dilution method as in Example 4. The MIC values of the P. cubeba extract against fluconazole resistant C. albicans strains (C. albicans$^{Fr}$ 10231) was found to be varying in the range of 0.01 to 0.06% (v/v).

The activity of the P. cubeba extract (in viscous oil form) against other Candida species, such as C. krusei$^{Fs}$ (fluconazole sensitive), C. krusei$^{Fr}$ (fluconazole resistant), C. glabrata$^{Fs}$ (fluconazole sensitive) and C. glabrata$^{Fr}$ (fluconazole resistant) strains was also determined by the macro broth dilution method as in Example 4. The MIC values of the P. cubeba oil extract against C. krusei$^{Fr}$ and C. krusei strains was found to be varying in the range of 0.06 to 0.12% (v/v) and 0.03 to 0.06% (v/v). The MIC values of the P. cubeba extract against C. glabrata$^{Fs}$ and C. glabrata$^{Fr}$ strains was found to be varying in the range of 0.06 to 0.12%(v/v) and 0.005 to 0.01% (v/v).

Example 6

In Vitro Susceptibility Testing (MIC) by Agar Dilution Method of Herbal Composition Formulated in Candy Form Five candies (approximately 15 g) were dissolved in saline and the oil globules were removed using a separating funnel. The oil globules were further heated to obtain an oily mass, which was dissolved in petroleum ether to separate the P. cubeba extract (in viscous oil form) from the remaining insoluble ingredients. The petroleum ether was evaporated and the extract (in viscous oil form) was used for the assay. The extract was further mixed with 5 ml of Sabouraud Dextrose Agar (SAB) medium containing Tween 20 (0.001%) and 1.2% agar.

A loopful of culture from 24-hour old slant (37° C.) was suspended in saline and vortexed for 15 seconds. The cell density of this suspension was adjusted by adding more saline and standardised to a turbidity equivalent to that of a 0.5 McFarland Standard with a spectrophotometer at 530 nm, to yield a stock inoculum suspension of $1 \times 10^6$ to $5 \times 10^6$ cells/ml. The stock solution was further diluted 100 times to yield a stock inoculum suspension of $1 \times 10^3$ to $5 \times 10^3$ cells/ml. 10 µl of the culture suspensions prepared were spotted on the solidified plates and spots allowed to dry at room temperature. The plates were then incubated at 37° C. for a period of 24 hours. The MIC was defined as the lowest concentration of the extract for candy formulation giving no visible growth or causing almost complete inhibition of growth in the plates. The MIC of the P. cubeba extract in the candy formulation was found to be 2% (v/v).

Example 7

Comparative Study: In Vitro Susceptibility Testing (MIC) by Macro Broth Dilution Method of P. cubeba Extract vis-à-vis Tea Tree Oil A comparative study to determine the activity of the P. cubeba extract (in viscous oil form) vis-à-vis commercially available tea tree oil was carried out against C. albicans and fluconazole resistant *C. albicans* strains (*C. albicans*$^{Fr}$ 10231) strains using macro broth dilution assay method as described in Example 4. The activity of the *P. cubeba* extract (in viscous oil form) vis-à-vis the commercially available tea tree oil was also determined by the same method against other *Candida* species, such as *C. krusei*$^{Fs}$ (fluconazole sensitive), *C. krusei*$^{Fr}$ (fluconazole resistant), *C. glabrata*$^{Fs}$ (fluconazole sensitive) and *C. glabrata*$^{Fr}$ (fluconazole resistant) strains was also determined by the same method. The results of the comparative study are presented in the following Table 1.

TABLE 1

| Candida species | MIC (% v/v) | |
| --- | --- | --- |
| | *P. cubeba* extract (in viscous oil form) | Tea tree oil |
| *C. albicans* | 0.12 | 0.25 |
| *C. albicans*$^{Fr}$ 10231 | 0.01 | 0.25 |
| *C. krusei*$^{Fs}$ G06 | 0.03 | 0.06 |
| *C. krusei*$^{Fr}$ G03 | 0.06 | 0.06 |
| *C. glabrata*$^{Fs}$ H04 | 0.12 | 0.03 |
| *C. glabrata*$^{Fr}$ H05 | 0.01 | 0.25 |

$^{Fs}$ = Fluconazole sensitive strain;
$^{Fr}$ = Fluconazole resistant strain.

The results clearly indicate that the *P. cubeba* extract (in viscous oil form) has MIC values superior to the MIC values of the tea tree oil, against *C. albicans* and more particularly, against the fluconazole resistant strains of *C. albicans*. The results also indicate that the *P. cubeba* extract has MIC value superior to that of the tea tree oil against the fluconazole resistant strains of *C. glabrata*. The MIC value of the *P. cubeba* extract against the fluconazole resistant strains of *C. krusei* is comparable to that of the tea tree oil.

We claim:

1. An oral herbal composition for use in the treatment of oral candidiasis, said composition comprising 0.05 to 20% by weight of a petroleum ether extract of *Piper cubeba* (*P. cubeba*) berries in viscous oil form and at least one pharmaceutically acceptable excipient.

2. The oral herbal composition according to claim 1, wherein the oral candidiasis is the azole resistant candidiasis.

3. The oral herbal composition according to claim 1, wherein the composition is formulated in a form selected from the group consisting of a candy, a chewable tablet and an oral gel.

4. The oral herbal composition according to claim 1, wherein the oral candidiasis is caused by candida species selected from the group consisting of *Candida albicans*, *Candida krusei* and *Candida glabrata*.

5. The oral herbal composition according to claim 1, wherein said pharmaceutically acceptable excipient is selected from the group consisting of a binder, lubricant, flavouring agent, sweetening agent, colouring agent, and preservative.

6. The oral herbal composition according to claim 5, wherein the binder is selected from the group consisting of starch paste, sorbitol, guar gum, polyvinyl pyrrolidone, hydroxy propylmethyl cellulose, sodium carboxymethyl cellulose and carbomer.

7. The oral herbal composition according to claim 5, wherein the lubricant is selected from the group consisting of magnesium, calcium and sodium stearates, stearic acid, talc, polyethylene glycols, sodium chloride and sodium benzoate.

8. The oral herbal composition according to claim 5, wherein the flavouring agent is selected from the group consisting of peppermint oil, menthol, lemon oil, orange oil and cinnamon oil.

9. The oral herbal composition according to claim 5, wherein the sweetening agent is selected from the group consisting of sucrose, liquid glucose, sucralose, mannitol, aspartame and saccharin sodium.

10. The oral herbal composition according to claim 3, wherein said composition is formulated in the form of a candy.

11. A process for manufacture of an oral herbal composition comprising a therapeutically effective amount of *Piper cubeba* (*P. cubeba*) extract and at least one pharmaceutically acceptable excipient; wherein said process comprises the steps of:
   a) obtaining the berries of *P. cubeba*;
   b) drying the *P. cubeba* berries in shade;
   c) pulverising the dried berries of *P. cubeba* to obtain a fine powder;
   d) extracting repeatedly the fine powder obtained in step (c) with petroleum ether;
   e) concentrating the extract under vacuum to obtain a concentrated liquid extract in viscous oil form; and
   f) formulating the extract which is in viscous oil form with at least one pharmaceutically acceptable excipient to obtain the oral herbal composition, said composition comprising 0.05 to 20% by weight of the extract.

12. The process according to claim 11, wherein petroleum ether is used in an amount two fold (weight/volume) the amount of the fine powder of *P. cubeba* berries.

13. The process according to claim 11, wherein the extraction is carried out at a temperature of about 35° C. to 40° C. and a pressure of about 1 atmosphere.

14. A method for the treatment of oral candidiasis in a subject, wherein said method comprises administering to the subject in need thereof a therapeutically effective amount of the oral herbal composition of claim 1.

15. The method according to claim 14, wherein the oral candidiasis is the azole resistant oral candidiasis.

16. The method according to claim 14, wherein said oral herbal composition is formulated in the form of a candy, chewable tablet and an oral gel.

17. The method according to claim 16, wherein said oral herbal composition is formulated in the form of a candy.

* * * * *